United States Patent [19]

Abood et al.

[11] Patent Number: 5,659,063
[45] Date of Patent: Aug. 19, 1997

[54] INTERMEDIATES FOR AMIDINO PHENYL PYRROLIDINE β-ALANINE UREA ANALOGS

[75] Inventors: Norman Anthony Abood, Morton Grove; Daniel Lee Flynn, Mundelein; Scott Anthony Laneman, Vernon Hills; Roger Nosal, Buffalo Grove; Lori Ann Schretzman, Gurnee, all of Ill.

[73] Assignee: G. D. Searle & Co., Chicago, Ill.

[21] Appl. No.: 467,417

[22] Filed: Jun. 6, 1995

Related U.S. Application Data

[62] Division of Ser. No. 349,333, Dec. 5, 1994.

[51] Int. Cl.⁶ .................... C07C 251/56; C07C 255/50
[52] U.S. Cl. ............................................ 558/414; 560/155
[58] Field of Search ........................ 548/543; 558/414; 560/155

[56] References Cited

U.S. PATENT DOCUMENTS

| | | | |
|---|---|---|---|
| 4,302,472 | 11/1981 | Cozzi et al. | 424/324 |
| 5,239,113 | 8/1993 | Bovy et al. | 562/440 |
| 5,344,957 | 9/1994 | Bovy et al. | 560/35 |

FOREIGN PATENT DOCUMENTS

WO94/22820   10/1994   WIPO .................. C07D 207/26

OTHER PUBLICATIONS

Friedinger et al., "Protected Lactam-Bridged Dipeptides for Use as Conformational Constraints in Peptides" *J. Org. Chem.*: 47, 104–109(1982).

Kottirsch et al. "Fibrinogen Receptor Antagonists Containing a Gamma-Lactam Gly-Asp Isostere" *Bioorganic & Medicinal Chemistry Letters*, vol. 3, No. 8, pp. 1675–1680 (1993).

D. H. Rich, J. P. Tam "A Convenient Synthesis of the Amino Acid, 1-Aminocyclopropane-1-carboxylic Acid", *Synthesis*, p. 46 (1978).

Kosaku Noda, et al. "A facile method for the preparation of t-butyloxycarbonylamino acid p-nitroanildes", *Int. J. Pept. Protein Res*,36 (2), pp. 197–200 (1990).

Norio Sugimoto et al. "3-Substituted 1-phenyl-1-pyrrolidinone", *Chemical Abstracts*,vol. 6, No. 5, Abstracts No. 5606, (1965).

*Primary Examiner*—David B. Springer
*Attorney, Agent, or Firm*—Cynthia S. Kovacevic; Roger A. Williams

[57] ABSTRACT

The invention herein is directed to a process for producing a lactam of the formula

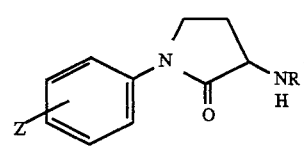

from a methionine analog of the formula

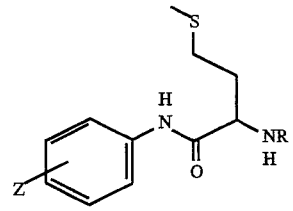

by treating the methionine analog with trimethylsulfonium halide or trimethylsulfoxonium halide in the presence of a base in a suitable aprotic solvent.

The invention herein is further directed to the preparation of amidinophenyl pyrrolidinyl β-alanine urea analogs using such methionine and lactam compounds as intermediates, which β-alanine urea analogs are useful as antithrombotics.

1 Claim, No Drawings

INTERMEDIATES FOR AMIDINO PHENYL PYRROLIDINE β-ALANINE UREA ANALOGS

This is a divisional application of co-pending application Ser. No. 08/349,333, filed on Dec. 5, 1994.

BACKGROUND OF THE INVENTION

The invention herein is directed to the cyclization of a methionine analog to a lactam using new reaction reagents and conditions. The invention herein is further directed to the enantioselective synthesis of ethyl 3-[[[[1-[4-(aminoiminomethyl)phenyl]-2-oxo-3(S)-pyrrolidinyl]amino]carbonyl]amino]propionate acetate and related β-alanine analogs. Such compounds are useful as antithrombotic agents.

More specifically the invention herein is directed to the conversion of a methionine analog such as

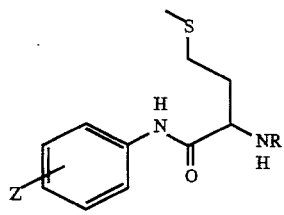

(Z=H, —CN, —CONH₂ or —CO₂Me)
to a lactam such as

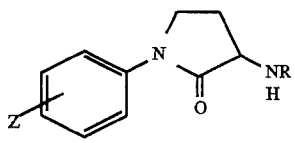

using reagent and reaction conditions which are beneficial in comparison to previously disclosed methodology for achieving such a conversion.

Friedinger et al., *J. Org. Chem.*, 47, (104–109), 1982 disclose general methods for the synthesis of lactam-constrained dipeptide analogs using three different paths from protected chiral α-amino acids to lactams. Included within this disclosure is a method for cyclizing methionine analogs to lactams via an alkylative cyclization involving a two step procedure using highly volatile and toxic methyl iodide and highly reactive sodium hydride as reagents.

It would be desirable to provide a process for conversion of a methionine analog to a lactam via conditions which do not employ volatile, toxic or highly reactive reagents and which produces a lactam having high enantiomeric purity.

SUMMARY OF THE INVENTION

The invention herein is directed to a process for producing a lactam of the formula

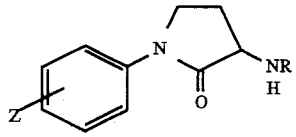

wherein R is a protecting group such as t-butoxycarbonyl (BOC) or carbobenzyloxy (CBZ) and Z is H, —CN, —CONH₂ or CO₂alkyl, from a methionine analog of the formula

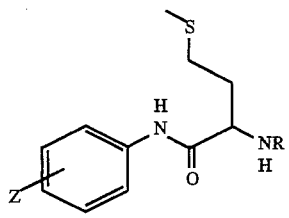

by treating the methionine analog with trimethylsulfonium halide or trimethylsulfoxonium halide in the presence of an inorganic or aminergic base, such as alkali metal hydroxides, alkoxides or carbonates or a tertiary amine, diazabicycloundecane (DBU), or Hunig's base [diisopropylethylamine (DIEA)], in a suitable aprotic solvent.

The invention herein is further directed to the preparation of amidinophenyl pyrrolidinyl β-alanine urea analogs using such methionine and lactam compounds as intermediates, which β-alanine urea analogs are useful as antithrombotics.

DETAILED DESCRIPTION OF THE INVENTION

The invention herein is directed to a process for producing a lactam of the formula

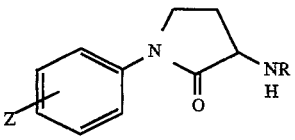

wherein R is a protecting group such as t-butoxycarbonyl (BOC) or carbobenzyloxy (CBZ) and Z is H, —CN, —CONH₂ or CO₂alkyl from a methionine analog of the formula

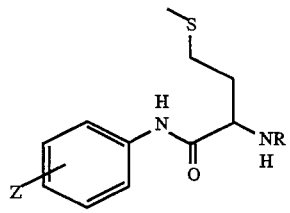

by treating the methionine analog with trimethylsulfonium halide or trimethylsulfoxonium halide (such as trimethylsulfonium iodide or trimethylsulfoxonium chloride) in the presence of an inorganic or aminergic base in a suitable aprotic solvent.

The invention herein is further directed to the preparation of amidinophenyl pyrrolidinyl β-alanine urea analogs using such methionine and lactam compounds as intermediates, which β-alanine urea analogs are useful as anti-thrombotics. Such process includes treating a methionine analog of the formula

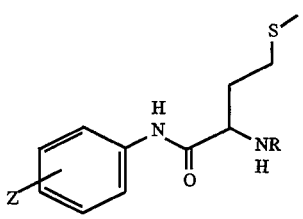

(wherein Z is —CN or —CONH₂) with trimethylsulfonium halide or trimethylsulfoxonium halide in the presence of a base, preferably potassium carbonate, in an aprotic solvent, preferably DMSO, to afford a lactam of the formula

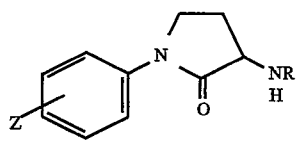

dehydrating when Z is —CONH₂ and deprotecting the lactam, reacting the resulting product with a β-amino ester in the presence of CDI to produce a urea of the formula

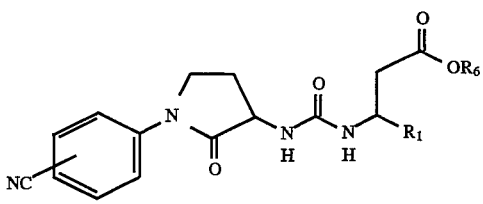

treating the urea with hydroxylamine to produce an amidoxime, hydrogenating the amidoxime; and isolating a compound of the formula

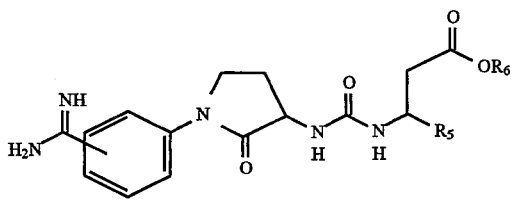

wherein $R_1$ is hydrogen, alkyl, aryl, arylalkyl, a heterocyclyl radical containing 1 to 3 heteroatoms or a heterocyclylalkyl and $R_6$ is selected from alkyl, aryl, arylalkyl or acyloxymethyl.

The general synthetic scheme is outlined in Scheme 1. Starting from commercially available materials, a suitably protected methionine (R=BOC, CBZ) is condensed with a substituted or unsubstituted aniline in the presence of a suitable amino acid coupling reagent (e.g. isobutyl chloroformate, 2-chloro-1-methylpyridinium iodide, 1,1'-carbonyldiimidazole (CDI) or 1-(3-dimetbylaminopropyl)-3-ethylcarbodiimide hydrochloride) and a tertiary amine base (e.g. N-methylmorpholine, N-methylpiperazine or trimethylamine) in a suitable aprotic solvent (e.g. dimethylformamide (DMF), tetrahydrofuran (THF) or $CH_2Cl_2$) at a temperature ranging from −15° C. to 25° C. to give the methionine analog 1.

Methionine analog 1 is cyclized to lactam 2 via a novel set of reaction conditions. Treatment of compound 1 with trimethylsulfonium halide or trimethylsulfoxonium halide in the presence of an inorganic or aminergic base (e.g. alkali metal hydroxide, alkali metal alkoxides, alkali metal carbonates or tertiary amines such as DBU or Hunig's base), preferably in the presence of potassium carbonate in a suitable aprotic solvent (e.g. DMF, dimethylacetamide (DMA), DMSO or THF) at a temperature ranging from 35° C. to 90° C. affords lactam 2. Historically, this conversion was accomplished by an alkylative cyclization in a two step procedure requiring highly volatile and toxic methyl iodide and highly reactive sodium hydride respectively as the principle reagents [c.f. Freidinger, R. M. et al., *J. Org. Chem.*, 47, 104–109 (1982); Kottirsch, G. et al., *Bioorg. Med. Chem. Letters*, 3, 1675–1680 (1993)]. Further, the extent of racemization in the later process was dependant upon the workup conditions. In the present invention, neither strong alkylators nor strong bases are required and the product is produced having high enantiomeric purity.

The lactam 2 can be dehydrated when Z is —CONH₂ to the nitrile 3 using standard reagents (e.g. trifluoroacetic anhydride (TFAA), trichloroacetic anhydride or thionyl chloride) in the presence of an amine base (e.g. $Et_3N$, pyridine, N-methylmorpholine or N,N-diisopropylethylamine) in an aprotic solvent (e.g. THF, EtOAc, pyridine or DME).

Aromatic analogs of methionine undergo cyclization as illustrated in Table 1. For example, the nitrile compound 1b, prepared by dehydrating 1a (TFAA, $Et_3N$), was cyclized to lactam 10. Also, the carbomethoxyanilides 1d and 1e undergo cyclization without subsequent hydrolysis of the ester function. This is important to note since ester containing intermediates cyclized under the Freidinger conditions undergo hydrolysis of the ester.

TABLE 1

| compound | compound, yield |
|---|---|
| 1a, Z = 4-CONH₂ | 2a, 75% |
| 1b, Z = 4-CN | 10, 88% |
| 1c, Z = 4-H | 2c, 38% |
| 1d, Z = 3-CO₂Me | 2d, 53% |
| 1e, Z = 4-CO₂Me | 2e, 79% |

Deprotection of the protecting group R with HCl or trifluoroacetic acid (TFA) (R=BOC) or $H_2$, Pd/C (R=CBZ) affords aminolactam 4. For R=BOC, excess anhydrous HCl or concentrated HCl (2.0–5.0 equivalents) in solvent (e.g. EtOAc, MeO-t-Bu, 1,4-dioxane or THF) at 5° to 50° C. for 0.5–23 hours affords product as the hydrochloride salt. Additionally the free base could be isolated as a precipitate by adding 1 equivalent of base (e.g. 1N NaOH) to an aqueous solution of the hydrochloride salt.

Synthesis of the urea product 5 is accomplished by sequential addition of an appropriate β-amino ester and aminolactam 4 to a suitable phosgene equivalent (e.g. triphosgene, diphosgene, phosgene, 1,1'-carbonyldiimidazole) in a suitable solvent (e.g. $CH_2Cl_2$, $CHCl_3$, $ClCH_2CH_2Cl$, DMF, DMA, pyridine, dioxane, THF, benzene, toluene). Reaction of 5 with hydroxylamine hydrochloride in the presence of a suitable base (e.g. Et₃N, (i-Pr)₂NEt, NaOAc, NaOEt, NaOH) in a suitable solvent (e.g. MeOH, EtOH, H₂O, DMF, DMA) provides the amidoxime intermediate 6. This material is hydrogenolyzed in the presence of a suitable catalyst (e.g. Pd/C, Pt/C, Pd(OH)₂) in a suitable solvent (e.g. MeOH, EtOH, i-PrOH or HOAc) in the presence of an acid counterion (e.g. HOAc, HCl, HBr, methanesulfonic acid (MsOH), succinic acid, citric acid, H₃PO₄, malic acid) affording the target compound 7 as the corresponding acid salt.

SCHEME 1

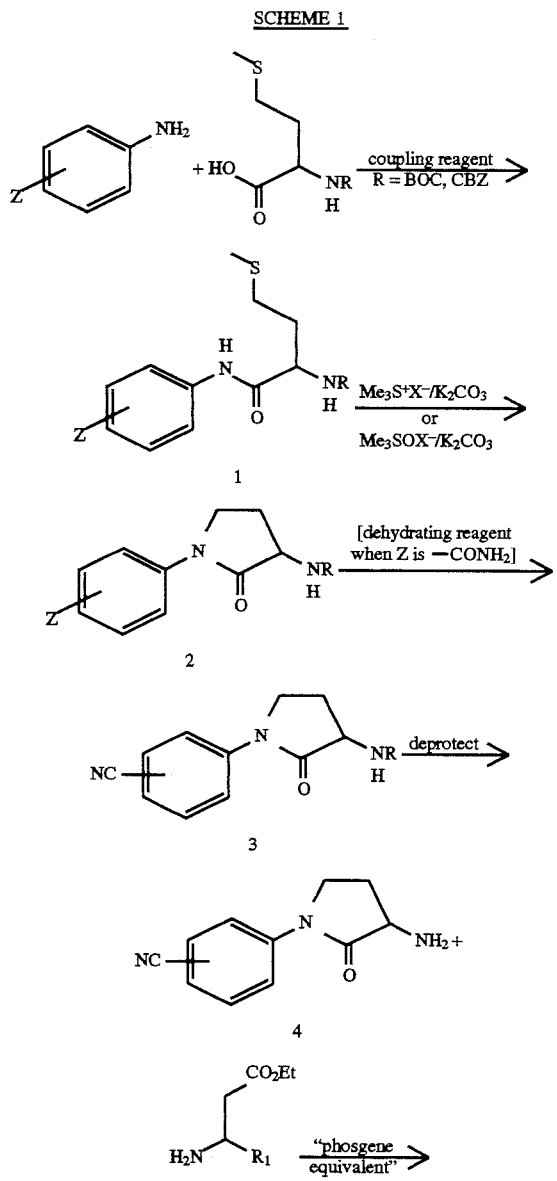

-continued
SCHEME 1

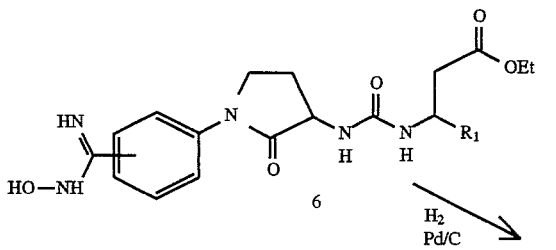

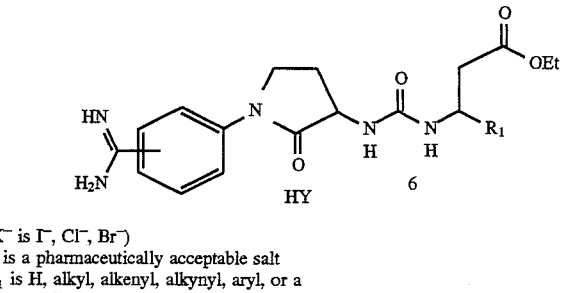

(X⁻ is I⁻, Cl⁻, Br⁻)
Y is a pharmaceutically acceptable salt
R₁ is H, alkyl, alkenyl, alkynyl, aryl, or a monocyclic heterocyclyl containing 1 to 30 O/N/S)

The preferred method of preparing a preferred antithrombotic agent, namely, ethyl 3-[[[[1-[4-(aminoiminomethyl)phenyl]-2-oxo-3(S)-pyrrolidinyl]amino]carbonyl]amino]propionate acetate is illustrated in Scheme 2 and Scheme 2a. Treatment of commercially available N-BOC-L-methionine and 4-aminobenzamide with 2-chloro-1-methylpyridinium iodide (CMPI) and N-methylmorpholine (NMM) in DMF affords the methionine amide 1A.

In the novel cyclization step, heating a mixture of 1A, trimethylsulfonium iodide and powdered K₂CO₃ (potassium carbonate) in DMSO at 70° C. gives the chiral lactam 2A.

Formation of the nitrile 10 is carried out by dehydrating the primary amide with a standard reagent (trifluoroacetic anhydride/Et₃N) in THF. Removal of the BOC protecting group with HCl/EtOAc affords the amine hydrochloride 11. Sequential addition of β-alanine ethyl ester hydrochloride and compound 11 to 1,1'-carbonyldiimidazole in DMF/pyridine (1:1) affords the unsymmetrical urea 12.

Treatment of 12 with hydroxylamine hydrochloride/triethylamine in ethanol gives the benzamidoxime 13. Hydrogenolysis of 13 with 4% palladium on carbon in acetic acid gives the target compound 14 as the acetate salt.

In Scheme 2B another preferred method is illustrated, wherein intermediate 1A is dehydrated to intermediate 1B. Subsequent cyclization of 1B to 10 is accomplished as described for the conversion of 1A to 2A. Intermediate 10 is then utilized further as demonstrated in Scheme 2 and 2a.

SCHEME 2

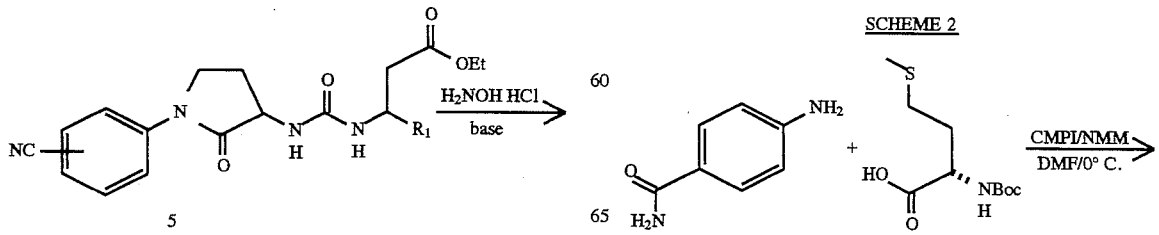

-continued
SCHEME 2
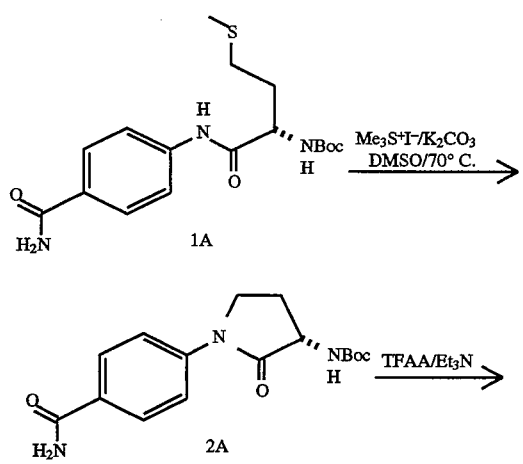
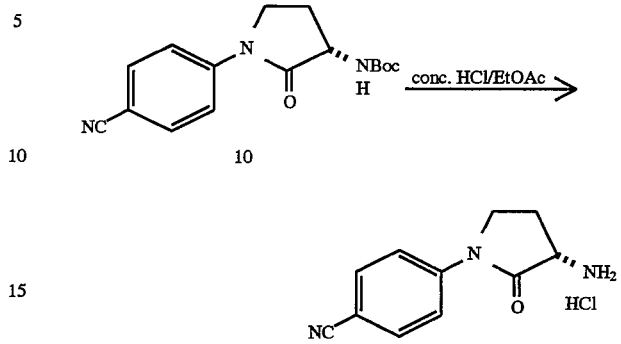
SCHEME 2a
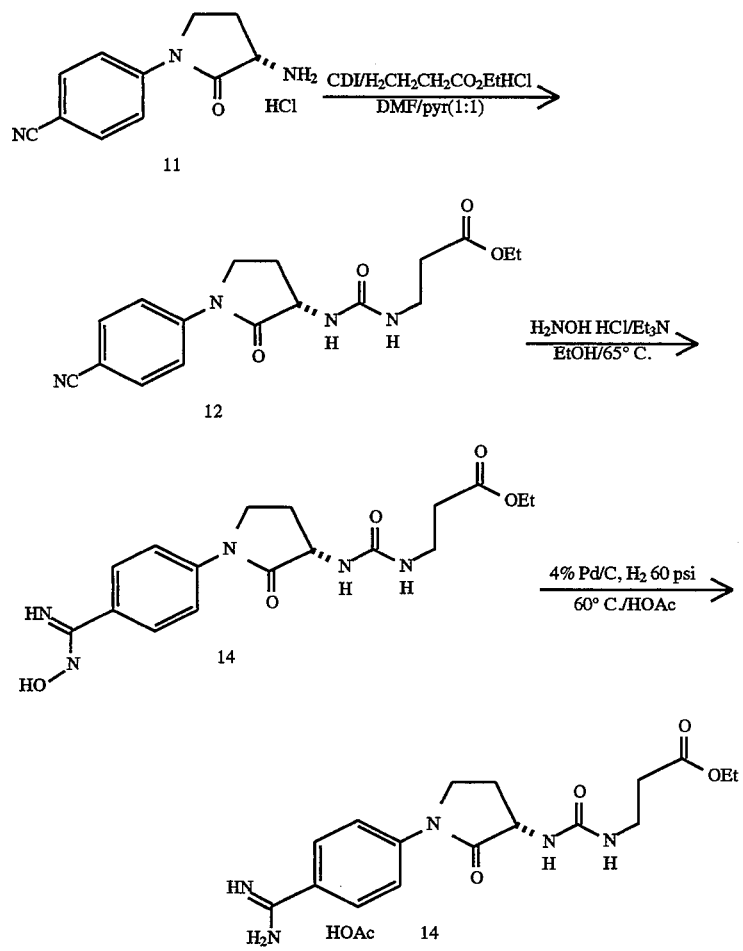

SCHEME 2b

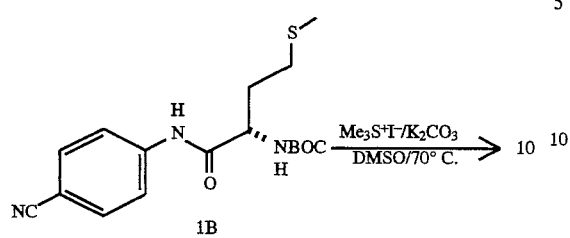

SCHEME 4

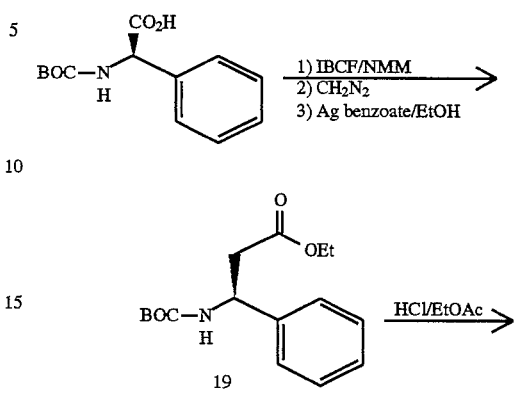

As illustrated in Scheme 3, classical resolution of commercially available ethyl 3-aminobutanoate with (R)-mandelic acid affords enantiomerically pure mandelate salt 15 after three recrystallizations from EtOAc. Sequential treatment of a suspension of 1,1'-carbonyldiimidazole with 11 then 15 affords the unsymmetrical urea 16. Treatment of 16 with hydroxylamine hydrochloride/triethylamine gives the benzamidoxime 17 which undergoes hydrogenolysis in HOAc to give the target compound 18.

SCHEME 3

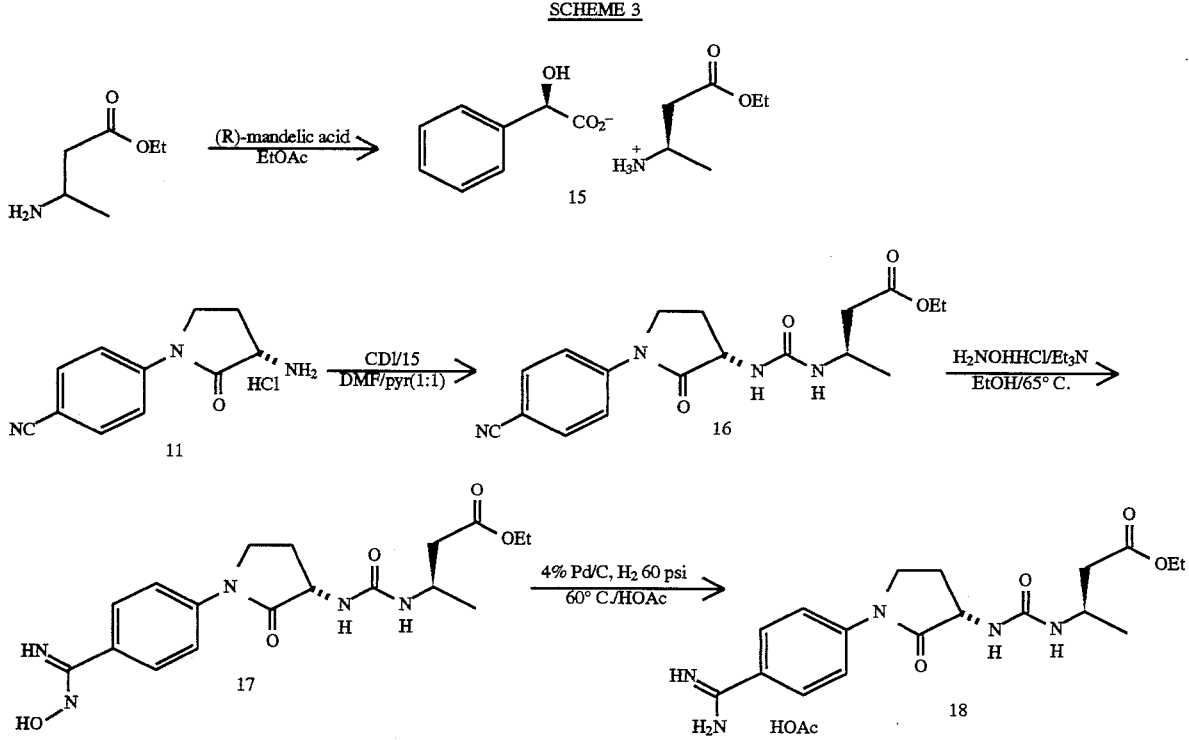

The Arndt-Eistert homologation (Scheme 4) of N-BOC-D-phenylglycine affords the chiral β-amino ester 19. Treatment of 19 with dry HCl affords the amine hydrochloride 20. Elaboration of 20 as outlined in Scheme 2a affords the target compound 21.

-continued
SCHEME 4

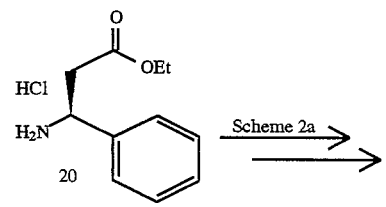

-continued
SCHEME 4

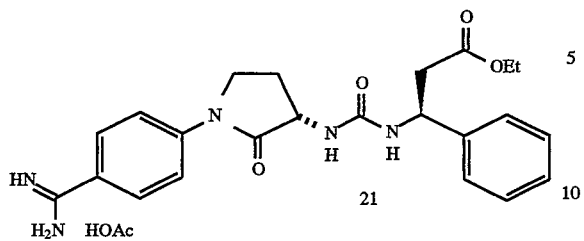

The β-amino acids and esters can be purchased or prepared from commercially available starting materials using known methods as illustrated in Scheme 5. The racemic β-heteroaryl β-amino acids can be prepared from the appropriate aryl aldehyde, malonic acid, and ammonium acetate (Method 1) [Johnson and Livak, *J. Am. Chem. Soc.*, 229 (1936)]. The racemic β-alkyl β-amino acids can be prepared from the corresponding alkene and chlorosulfonyl isocyanate (CSI) which goes through the β-lactam as shown in Method 2 [W. A. Szabo, *Aldrichimica Acta*, 23 (1977); R. Graf, *Anqew. Chem. Int. Ed.*, 172 (1968)]. The β-lactam can be opened to the ethyl ester by treatment with anhydrous HCl in ethanol. An alternative method to form racemic β-amino esters is shown in Method 3. Nucleophiles can be added to 4-benzoyloxy-2-azetidinone to afford a variety of 3-substituted β-amino esters after treatment with anhydrous HCl in ethanol [K. Prasad et al., Vol. 19, *Heterocycles*, 2099 (1982)]. The racemic β-amino acids and esters can be resolved using classical methods described in the literature [E. Fischer, H. Scheibler, R. Groh, Ber., 2020 (1910); E. Fischer, H. Scheibler, *Annalen*, 337 (1911)].

Chiral β-amino acids and esters can also be prepared using many different approaches including the following methods: 1) homologation of suitably protected α-amino acids using the Arndt-Eistert reaction as shown in Method 4 [Meier and Zeller, *Angew. Chem. Int. Ed.*, 32–43 (1975); M. Rodriguez et al., *Tetrahedron Lett.*, 5153 (1990); W. J. Greenlee, *J. Med. Chem.* 434 (1985) and references therein], 2) through the addition of an amine to α,β-unsaturated esters bearing a chiral auxiliary as shown in Method 5 [J. d'Angelo, J. Maddaluno, *J. Am. Chem. Soc.*, 8112–14, (1986)], 3) through an enantioselective hydrogenation of a dehydroamino acid as shown in Method 6 [see: Asymmetric Synthesis, Vol 5, (J. D. Morrison, Ed.) Academic Press, New York, 1985], and 4) through the addition of enantiomerically pure amines to α,β-unsaturated esters as shown in Method 7 [S. G. Davies, O. Ichihara, *Tetrahedron: Asymmetry*, 183–186 (1991)].

SCHEME 5

Method 1

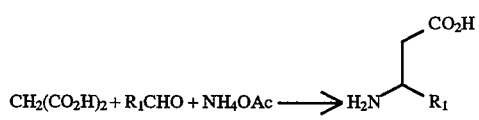

($R_1$ is aryl or heteroaryl)

Method 2

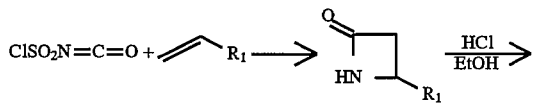

-continued
SCHEME 5

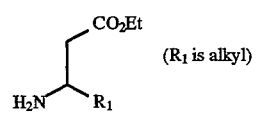

($R_1$ is alkyl)

Method 3

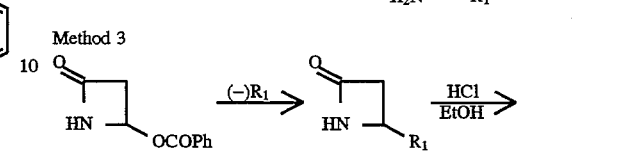

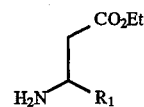

($R_1$ is alkyl, aryl, heterocyclyl, alkenyl, alkynyl)

Method 4

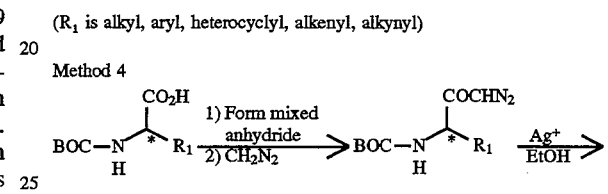

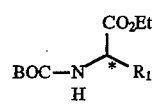

Retention of stereochemistry

*Indicates Chiral Center
($R_1$ is alkyl, aryl, heterocyclyl, arylalkyl, heteroarylalkyl)

Method 5

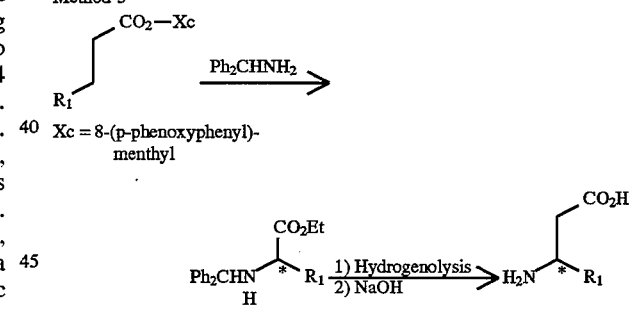

Xc = 8-(p-phenoxyphenyl)-menthyl ($R_1$ is alkyl, aryl, arylalkyl, heterocyclyl, heteroarylalkyl)

Method 6

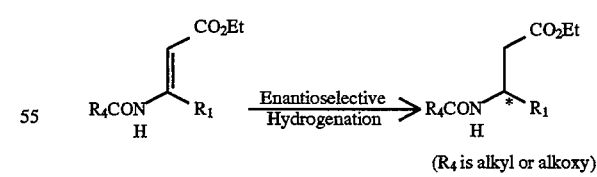

($R_4$ is alkyl or alkoxy)

*Indicates Chiral Center
($R_1$ is alkyl, aryl, arylalkyl)

Method 7

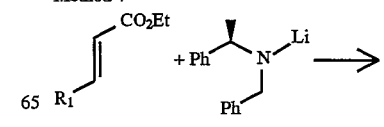

-continued
SCHEME 5

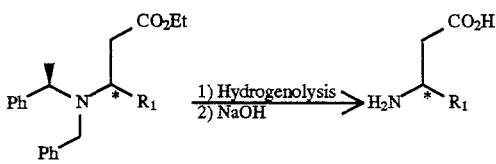

(R₁ is alkyl, aryl, heterocyclyl, arylalkyl, heteroarylalkyl)

As used herein the term "lower alkyl" refers to a straight or branched chain hydrocarbon radical having from 1 to about 6 carbon atoms. Examples of such "lower alkyl" radicals are methyl, ethyl, n-propyl, isopropyl, n-butyl, isobutyl, sec-butyl, t-butyl, pentyl, neo-pentyl, hexyl, isohexyl and the like.

As used herein the term "lower alkenyl" refers to unsaturated acyclic hydrocarbon radicals containing at least one double bond and 2 to about 6 carbon atoms. Examples of such groups include, ethenyl, propenyl, butenyl, isobutenyl, pentenyl, hexenyl and the like.

As used herein the term "lower alkynyl" refers to unsaturated acyclic hydrocarbon radicals containing one or more triple bonds and 2 to about 6 carbon atoms. Examples of such groups are ethynyl, propynyl, butynyl, pentynyl, hexynyl and the like.

The term aryl as used herein denotes carbocyclic aromatic ring systems composed of one or more aromatic rings. Preferred aryl groups are those consisting of one, two or three benzene rings. The term embraces aromatic radicals such as phenyl, naphthyl and biphenyl.

The term acyloxymethyl embraces groups of the formula

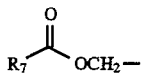

wherein R₇ is alkyl or aryl as defined above.

As used herein the phrase "heterocyclyl radical containing 1 to 3 heteroatoms" refers to monocyclic or bicyclic radicals wherein 1 to 3 carbon atoms have been replaced with a heteroatom selected from oxygen, nitrogen or sulfur. Such rings can be saturated or unsaturated and include heteroaromatics.

The following non-limiting examples describe and illustrate methods for carrying out the process of the present invention, as well as other aspects of the present invention, and the results achieved thereby in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes described in these examples can be used to perform the process of the present invention.

Unless otherwise indicated all starting materials and equipment employed were commercially available.

EXAMPLE 1

Preparation of N-[(4-aminocarbonyl)phenyl]-4-methylthio-2(S)-[[(1,1-dimethylethoxy)carbonyl]amino]butanamide (1A).

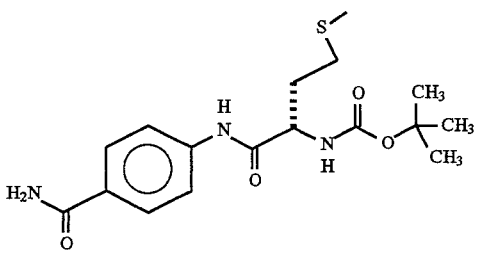

A. To a solution of L-BOC-methionine (100.0 g, 0.40 mol), 4-aminobenzamide (57.3 g, 0.42 mol) and CMPI (102.6 g, 0.40 mol) in 250 ml of DMF at 0° C., under nitrogen, was added NMM (88 mL, 0.8 mol) over two minutes. The reaction mixture was stirred and allowed to gradually warm to room temperature while stirring for 4 hours. The reaction was quenched by the addition of 0.1 N HCl (750 mL) over about 10 minutes. After stirring for about 30 minutes, the white precipitate was filtered, washed with H₂O and dried affording 123.3 g (84%) of product [m.p. 193.5°–195° C. (dec.)].

$[\alpha]_D^{25} = -23.0°$ (MeOH, c=10.85 mg/ml)

Anal. calc'd. for $C_{17}H_{25}N_3O_4S \cdot 0.33H_2O$:

Calc'd.: C, 54.67; H, 6.93; N, 11.25; S, 8.59.

Found: C, 54.63; H, 7.02; N, 11.05; S, 8.63.

B. The following compounds were made in a like manner substituting other anilines for 4-aminobenzamide:

N-phenyl-4-methylthio-2(S)-[[(1,1-dimethylethoxy)carbonyl]amino]butanamide (1c), ¹H-NMR (300 MHz, CD₃OD) δ 1.44 (s, 9H), 1.90–2.05 (m, 2H), 2.08 (s, 3H), 2.58 (m, 2H), 4.34 (m, 1H), 7.08 (t, J=8 Hz, 1H), 7.29 (t, J=8 Hz, 2H), 7.57 (d, J=8 Hz, 2H).

N-[(3-methoxycarbonyl)phenyl]-4-methylthio-2(S)-[[(1,1-dimethylethoxy)carbonyl]amino]butanamide (1d), ¹H-NMR (300 MHz, CDCl₃) δ 1.43 (s, 9H), 2.00–2.25 (m, 2H), 2.08 (s, 3H), 2.63 (m, 2H), 3.82 (s, 3H), 4.65 (m, 1H), 6.18 (d, J=7 Hz, 1H, exchangeable), 7.24 (t, J=8 Hz, 1H), 7.71 (m, 2H), 8.19 (s, 2H), 9.58 (s, 1H, exchangeable).

N-[(4-methoxycarbonyl)phenyl]-4-methylthio-2(S)-[[(1,1-dimethylethoxy)carbonyl]amino]butanamide (1e), ¹H-NMR (300 MHz, CDCl₃) δ 1.42 (s, 9H), 2.00–2.25 (m, 2H), 2.10 (s, 3H), 2.64 (m, 2H), 3.90 (s, 3H), 4.62 (m, 1H), 6.03 (d, J=7 Hz, 1H, exchangeable), 7.58 (d, J=8 Hz, 2H), 7.88 (d, J=8 Hz, 2H), 9.53 (s, 1H, exchangeable).

C. Preparation of N-(4-cyanophenyl)-4-methylthio-2(S)-[[(1,1-dimethylethoxy)carbonyl]amino]butanamide (1b), To an ice cooled, stirred suspension of compound 1a (10.00 g, 27.23 mmol) and triethylamine (16.5 g, 0.163 mol) in 40 mL of THF was added TFAA (7.88 g, 37.53 mmol) at a rate to keep the internal temperature between 5°–10° C. The resulting solution was stirred at 0° C. for 20 minutes then quenched at 0° C. by slowly adding 45 mL of 2N HCl. After the subsequent addition of 40 mL of saturated NaCl, the mixture was extracted with EtOAc, washed with saturated NaHCO₃, dried (MgSO₄), treated with decolorizing charcoal (ca. 1g) and filtered through a bed of silica gel using EtOAc as eluent. Removal of the solvent under reduced pressure produced a golden yellow oil which was dried to 9.50 g of a gummy foam under high vacuum. ¹H-NMR (300 MHz, CDCl₃) δ 1.47 (s, 9H), 2.02 (m, 2H), 2.13 (s, 3H), 2.18 (m, 1H), 2.63 (t, J=7 Hz, 2H), 4.44 (m, 1H), 5.34 (broad, 1H, exchangeable), 7.57 (d, J=8 Hz, 2H), 7.63 (d, J=8 Hz, 2H), 9.07 (s, 1H, exchangeable).

EXAMPLE 2

Preparation of 1-[(4-aminocarbonyl)phenyl]-3(S)-[[1,1-dimethlethoxy)carbonyl]amino]pyrrolidin-2-one (2a)

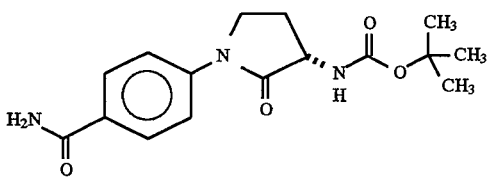

A. To a solution of the product of example 1a (3.00 g, 8.16 mmol) in DMSO (6 mL) was added trimethylsulfonium iodide (5.00 g, 24.48 mmol) and powdered $K_2CO_3$ (1.69 g, 12.24 mmol). The reaction mixture was stirred at 80° C. under nitrogen for 3 hours, cooled to room temperature and diluted with $H_2O$ (30 mL). The white precipitate was filtered, washed with $H_2O$ and dried affording 1.94 g (75%) of product which was used directly in the preparation of the compound of Example 3. An analytical sample was prepared by recrystallizing the product from 1 part hot i-PrOH and diluting with 3 parts $H_2O$ [m.p. 225°–226° C. (dec)].

$[\alpha]_D^{25}=-14.1°$ (MeOH, c=9.90 mg/mL)
Anal. calc'd. for $C_{16}H_{21}N_3O_4 \cdot 1\ H_2O$:
Calcd.: C, 56.96; H, 6.87; N, 12.46.
Found: C, 56.78; H, 6.56; N, 12.36.

B. The following compounds were made in a like manner substituting other products of Example 1 (1b–1e) for Compound 1a:

N-(4-cyanophenyl)-3(S)-[[(1,1-dimethylethoxy)carbonyl]amino]pyrrolidin-2-one (3), $^1$H-NMR (300 MHz, $CDCl_3$) δ 1.47 (s, 9H), 2.08 (m, J=1H), 2.80 (m, 1H), 3.82 (m, 2H), 4.38 (m, 1H), 5.20 (broad s, 1H, exchangeable), 7.68 (d, J=8 Hz, 2H), 7.82 (d, J=8 Hz, 2H).

N-phenyl-3(S)-[[(1,1-dimethylethoxy)carbonyl]amino]pyrrolidin-2-one (2c), $^1$H-NMR (300 MHz, $CDCl_3$) δ 1.43 (s, 9H), 2.00 (m, 1H), 2.80 (m, 1H), 3.81 (m, 2H), 4.36 (m, 1H), 5.23 (broad, 1H, exchangeable), 7.18 (t, J=8 Hz, 1H), 7.39 (t, J=8 Hz, 2H), 7.64 (d, J=8 Hz, 2H).

N-[(3-methoxycarbonyl)phenyl]-3(S)-[[(1,1-dimethylethoxy)carbonyl]amino]pyrrolidin-2-one (2d), $^1$H-NMR (300 MHz, $CDCl_3$) δ 1.47 (s, 9H), 2.04 (m, 1H), 2.80 (m, 1H), 3.85 (m, 2H), 3.93 (s, 3H), 4.38 (m, 1H), 5.23 (broad, 1H, exchangeable), 7.47 (t, J=8 Hz, 1H), 7.86 (m, 1H), 8.10 (m, 2H).

N-[(4-methoxycarbonyl)phenyl]-3(S)-[[(1,1-dimethylethoxy)carbonyl]amino]pyrrolidin-2-one (2e), $^1$H-NMR (300 MHz, $CDCl_3$) δ 1.48 (s, 9H), 2.04 (m, 1H), 2.80 (m, 1H), 3.83 (m, 2H), 3.92 (s, 3H), 4.38 (m, 1H), 5.20 (broad, 1H, exchangeable), 7.75 (d, J=8 Hz, 2H), 8.06 (d, J=8 Hz, 2H).

EXAMPLE 3

Preparation of 1-(4-cyanophenyl)-3(S)-[[(1,1-dimethylethoxy)carbonyl]amino]pyrrolidin-2-one.

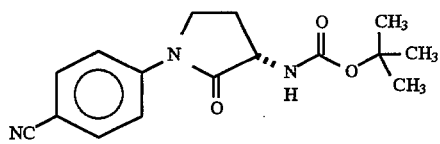

To a suspension of the product of example 2a (2.0 g, 6.27 mmol) and triethylamine (5.23 mL, 37.6 mmol) in THF (20 mL) at 0° C. was added neat trifluoroacetic anhydride (3.87 g, 18.8 mmol) dropwise over 5 minutes. The solution was stirred at 0° C. for an additional 1 hour, warmed to room temperature then quenched by adding 20 mL of water. The reaction mixture was partially concentrated to approximately ½ the volume of THF whereupon the product precipitated. The precipitate was filtered, washed with water and dried affording 1.60 g (85%) of product (m.p. 152°–153.5° C.).

$[\alpha]_D^{25}=-11.4°$ (MeOH, c=9.65 mg/mL)
Anal. calc'd. for $C_{16}H_{19}N_3O \cdot 1\ H_2O$:
Calc'd.: C, 60.17; H, 6.63; N, 13.16.
Found: C, 59.75; H, 6.30; N, 13.14.

EXAMPLE 4

Preparation of 1-(4-cyanophenyl)-3(S)-aminopyrrolidin-2-one Hydrochloride.

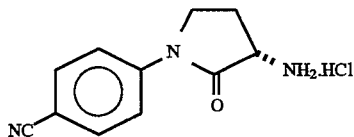

HCl gas was bubbled through a solution of the product of example 3 (62.0 g, 206 mmol) in EtOAc (750 mL) at ambient temperature for 15 minutes. After an additional 30 minutes, the precipitated product was filtered, washed with EtOAc and dried affording 46.7 g (96%) [m.p. 253°–254.5° C. (dec.), >99.9% e. e.]. Enantiomeric purity was determined by chiral HPLC analysis using a Crownpak CR(–) column (15 cm×4.0 mm) and isocratic elution with 1% aqueous $HClO_4$ at 1.2 mL/min. The detector was set at 254 nm.

$[\alpha]_D^{25}=-20.8°$ (MeOH, c=10.63 mg/mL)
Anal. calc'd. for $C_{11}H_{12}N_3OCl \cdot 1/4H_2O$:
Calculated: C, 54.55; H, 5.20; N, 17.35.
Found: C, 54.51; H, 4.98; N, 17.40.

EXAMPLE 5

Preparation of Ethyl 3-[[[[1-4-cyanophenyl)-2-oxo-3(S)-pyrrolidinyl]amino]carbonyl]amino]propionate.

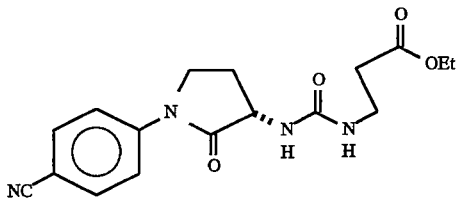

To a suspension of 1,1'-carbonyldiimidazole (572 mg, 3.55 mmol) in pyridine (2.5 mL) at 5° C. under nitrogen was added solid ethyl 3-amino-propionate hydrochloride (545 mg, 3.55 mmol). The resulting solution was stirred at 5° C. for 15 minutes, diluted with 2.5 mL of DMF and removed from the ice bath. The product of example 4 (700 mg, 2.96 mmol) was added all at once and the reaction mixture was stirred at 75°–80° C. for 2 hours. After cooling to room temperature, the resulting solution was diluted with 15 mL of 1 N HCl. The white precipitate was filtered, washed with $H_2O$ and dried. Trituration and filtration from methyl t-butyl ether afforded 844 mg of product (m.p. 168.5°–169° C.). Extractive work up of the filtrate with EtOAc afforded an additional 110 mg of product (94% overall).

$[\alpha]_D^{25}=+9.5°$ (MeOH, c=9.45 mg/mL)
Anal. calc'd. for $C_{17}H_{20}N_4O_4$:

Calculated: C, 59.29; H, 5.85; N, 16.27.
Found: C, 58.94; H, 5.71; N, 16.13.

EXAMPLE 6

Preparation of Ethyl 3-[[[[1-[4-(amino(hydroxyimino)-methyl)phenyl]-2-oxo-3(S)-pyrrolidinyl]amino]carbonyl]amino]propionate.

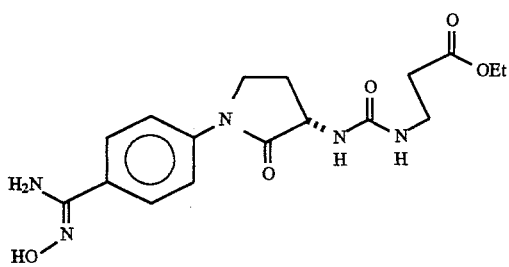

To a suspension of the product of example 5 (104 g , 304 mmol) and hydroxylamine hydrochloride (42 g, 607 mmol) in EtOH (900 mL) was added triethylamine (61 g, 607 mmol). The reaction mixture was heated to 60°–65° C. and stirred for 2 hours. The reaction mixture was concentrated under reduced pressure and diluted with H$_2$O. The precipitate was filtered, washed with H$_2$O and dried affording 110 g (96%) of product (m.p. 188°–190° C.).
[α]$_D^{25}$=–2.8 (MeOH, c=10.53 mg/mL)
Anal. calc'd. for C$_{16}$H$_{19}$N$_3$O: C, 54.10; H, 6.14; N, 18.56.
Found: C, 53.76; H, 6.14; N, 18.52.

EXAMPLE 7

Preparation of Ethyl 3-[[[[1-[4-(aminoiminomethyl)phenyl]-2-oxo-3(S)-pyrrolidinyl]amino]carbonyllaminolpropionate Acetate.

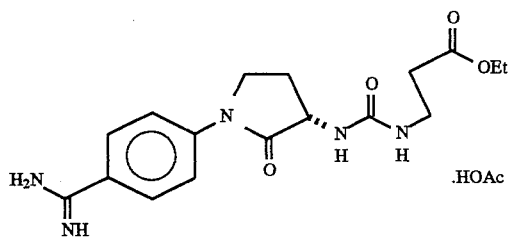

To a suspension of the product of example 6 (250 g, 663 mmol) in HOAc (1 L) was added 100 g of 4% Pd/C (50% wet). The mixture was hydrogenated at 60° C. using 60 psi H$_2$ for 1.37 hours. The catalyst was filtered and the solvent evaporated under reduced pressure. The syrupy product was diluted Sequentially while stirring with 500 mn MeOH, 1.5 L EtOH and 800 mL of C$_3$CN. The white solid was filtered, washed with CH$_3$CN and dried affording 219 g of product. The mother liquor was concentrated and the residue dissolved in H$_2$O and treated with decolorizing charcoal (5 g). After filtration and removal of the solvent under reduced pressure, the residue was dissolved in a minimal amount of HOAc and diluted sequentially with 150 mL of i-PrOH and 150 mL of C$_3$CN. The precipitate was filtered, washed with i-PrOH/CH$_3$CN (1:1) and dried affording an additional 35 g of product (91% overall) [m.p. 213°–214° C. (dec.)]. Enantiomeric purity was determined by chiral HPLC using a Chiralcel-OD column and EtOH/Heptane/TFA (20:80:0.1) as the mobile phase and was determined to be >99.9% e. e..
[α]$_D^{25}$=+13.2 (MeOH, c=9.43 mg/mL)

Anal. calc'd. for C$_{19}$H$_{27}$N$_5$O$_6$: C, 54.15; H, 6.46; N, 16.62.
Found: C, 54.08; H, 6.57; N, 16.57.

EXAMPLE 8

Preparation of Ethyl 3(R)-aminobutanoate (R)-mandelate.

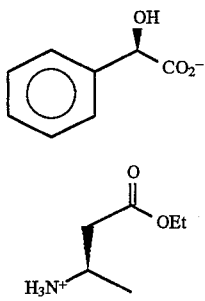

A solution of ethyl 3-aminobutyrate hydrochloride (4.5 g, 26.8 mmol) in 27 mL of 1N NaOH was extracted 2X with EtOAc. The organic fraction was dried (Na$_2$SO$_4$) and concentrated under reduced pressure. Recrystallization of the residue 3X from EtOAc afforded 1.93 g (51%) of product as a single chiral diastereomer as determined by NMR spectroscopy (m.p. 125°–125° C.). $^1$H-NMR (300 MHz, CDCl$_3$) δ 1.00 (d, J=7Hz, 3H), 1.27 (t, J=7Hz, 3H), 2.23–2.45 (m, 2H), 3.13 (m, 1H), 4.13 (q, J=7Hz, 2H), 4.85 (s, 1H), 7.17–7.33 (m, 3H), 7.41 (d, J=8Hz, 2H).

Anal. calc'd. for C$_{14}$H$_{21}$NO$_5$: C, 59.35; H, 7.47; N, 4.94.
Found: C, 59.03, H, 7.51; N, 4.83.

EXAMPLE 9

Preparation of Ethyl 3(R)-[[[[1-(4-cyanophenyl)-2-oxo-3(S)-pyrrolidinyl]-amino]carbonyl]amino]butanoate.

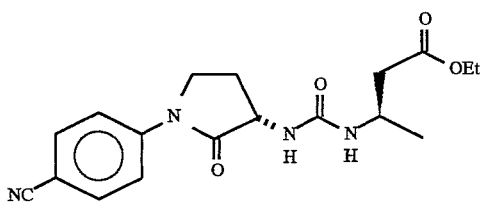

To a suspension of 1,1'-carbonyldiimidazole (178 mg, 1.1 mmol) in pyridine (2.5 mL) at 5° C. under nitrogen was added the product of example 4 (260 mg, 1.1 mmol). The resulting solution was stirred at 5° C. for 15 minutes, diluted with 2.5 mL of DMF and removed from the ice bath. The product of example 8 (375 mg, 1.32 mmol) was added all at once and the reaction mixture stirred at 75°–80° C. for 2 hours. After cooling to room temperature, the resulting solution was diluted EtOAc and washed with 1N HCl, saturated NaHCO$_3$ and dried (MgSO$_4$). Evaporation of the solvent afforded 295 mg (73%) of product (m.p. 177.5°–179° C.). $^1$H-NMR (300 MHz, CDCl$_3$) δ 1.20–1.30 (m, 6H), 2.05 (m, 1H), 2.53 (m, 2H), 2.83 (m, 1H), 3.83 (m, 2H), 4.15 (q, J=7Hz, 2H), 4.19 (m, 1H), 4.48 (m, 1H), 7.68 (d, J=8Hz, 2H), 7.82 (d, J=8Hz, 2H).

Anal. calc'd. for C$_{18}$H$_{22}$N$_4$O$_4$·0.1 H$_2$O:
Calculated: C, 60.02; H, 6.21; N, 15.56.
Found: C, 60.29; H, 6.21; N, 15.06.

EXAMPLE 10

Preparation of Ethyl 3(R)-[[[[1-[4-(amino(hydroxyimino)-methyl)phenyl]-2-oxo-3(S)-pyrrolidinyl]amino]carbonyl]amino]butanoate.

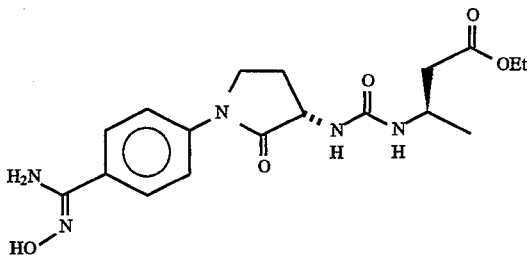

The title compound was prepared from the product of example 9 (250 mg, 0.63 mmol) in a manner similar to example 6 affording 203 mg (83%) of product [m.p. 165°–167° C. (dec.)]. $^1$H-NMR (300 MHz, $d_6$-DMSO) δ 1.06 (d, J=7Hz, 3H), 1.28 (t, J=7Hz, 3H), 1.88 (m, 1H), 2.30–2.53 (m, 3H), 3.75 (m, 2H), 3.95 (m, 1H), 4.05 (q, J=7Hz, 2H), 4.40 (m, 1H), 7.56 (s, 4H).

Anal. calc'd. for $C_{18}H_{25}N_5O_5 \cdot 1/3H_2O$:

Calculated: C, 54.40; H, 6.51; N, 17.64.

Found: C, 54.76; H, 6.71; N, 17.21.

EXAMPLE 11

Preparation of Ethyl 3(R)-[[[[1-[4-(aminoiminomethyl)phenyl]-2-oxo-3(S)-pyrrolidinyl]amino]carbonyl]amino]butanoate Acetate

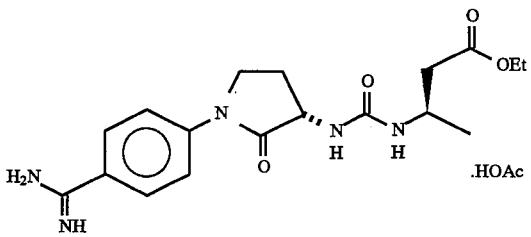

The title compound was prepared from the product of example 10 (150 mg, 0.38 mmol) in a manner similar to example 7 affording 131 mg (77%) of product [m.p. 208°–209° C. (dec.)].

$^1$H-NMR (300 MHz, $d_6$-DMSO) δ 1.08 (d, J=7Hz, 3H), 1.19 (t, J=7Hz, 3H), 1.39 (s, 3H), 1.94 (m, 1H), 2.30–2.53 (m, 3H), 3.80 (m, 2H), 3.95 (m, 1H), 4.06 (q, J=7Hz, 2H), 4.43 (m, 1H), 7.86 (d, J=8Hz, 2H), 7.91 (d, J=8Hz, 2H).

Anal. calc'd. for $C_{20}H_{29}N_5O_6 \cdot 3/4$ $H_2O$:

Calculated: C, 53.50; H, 6.85; N, 15.60.

Found: C, 53.34; H, 6.46; N, 15.35.

EXAMPLE 12

Preparation of Ethyl β(S)-[[(1,1-dimethylethoxy)carbonyl]amino]benzenepropanoate.

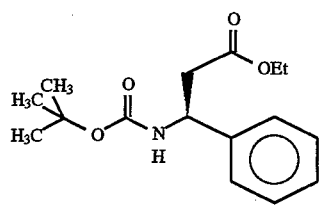

To a stirred solution of N-BOC-D-phenylglycine (5.02 g, 20 mmol), N-methylmorpholine (2.02 g, 20 mmol) in EtOAc (100 mL) at 0° C. was added isobutyl chloroformate (2.73 g, 20 mmol). After 15 minutes the reaction mixture was filtered to remove the amine salts then an ethereal solution of diazomethane (60 mL, 30 mmol) was added. The cooling bath was removed and the reaction mixture stirred at ambient temperature for 2 hours. The reaction mixture was purged with nitrogen for 15 minutes to remove the excess diazomethane. The reaction mixture was diluted with EtOAc, washed with 1N HCl, saturated $NaHCO_3$, and dried ($MgSO_4$). Evaporation of the solvent afforded the crude diazoketone which was dissolved in EtOH (100 mL) and then treated sequentially with $AgO_2CPh$ (1.6 g, 7 mmol) and triethylamine (6.06 g, 60 mmol). After 20 hours the reaction mixture was concentrated and chromatographed (silica gel, 15% EtOAc/hexanes) affording 4.90 g (85%) of product as a colorless oil. $^1$H-NMR (300 MHz, $CDCl_3$) δ 1.17 (t, J=7 Hz, 3H), 1.43 (s, 9H), 2.73–2.92 (m, 2H), 4.07 (q, J=7 Hz, 2H), 5.10 (m, 1H), 5.48 (m, 1H), 7.22–7.39 (m, 5H).

EXAMPLE 13

Preparation of Ethyl β(S)-aminobenzenepropanoate Hydrochloride.

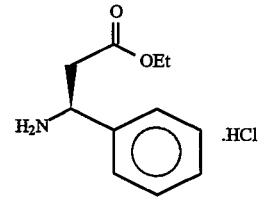

Dry HCl gas was bubbled through a solution of the product of example 12 (3.0 g, 10.2 mmol) in EtOAc (50 mL) at ambient temperature for 15 minutes. After stirring for an additional 30 minutes, the solvent was removed under reduced pressure affording 2.30 g (98%) of product as a yellow oil. $^1$H-NMR (300 MHz, $d_6$-DMSO) δ 1.03 (t, J=7Hz, 3H), 3.02 (dd, J=10Hz, J=15Hz, 1H), 3.25 (dd, J=6Hz, J=15Hz, 1H), 3.96 (m, 2H), 4.55 (m, 1H), 7.3–7.6 (m, 5H), 8.93 (s, 3H).

EXAMPLE 14

Preparation of Ethyl β(S)-[[[[1-(4-cyanophenyl)-2-oxo-3(S)-pyrrolidinyl]amino]carbonyl]amino]benzenepropanoate.

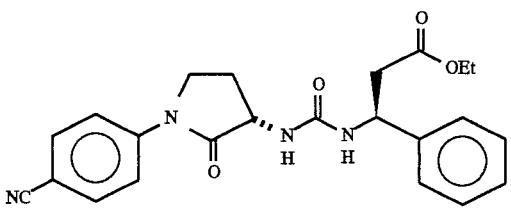

The title compound was prepared from the product of example 13 (685 mg, 2.9 mmol) and the product of example 4 (600 mg, 2.9 mmol) in a manner similar to example 5 affording 1.09 g (91%) of product (m.p. 108°–109° C.). $^1$H-NMR (300 MHz, CDCl$_3$) δ 1.16 (t, J=7Hz, 3H), 2.00 (m, 1H), 2.77–2.93 (m, 3H), 3.81 (m, 2H), 4.05 (q, J=7Hz, 2H), 4.50 (m, 1H), 5.26 (m, 1H), 7.20–7.35 (m, 5H), 7.66 (d, J=8Hz, 2H), 7.80 (d, J=8Hz, 2H).
Anal. calc'd. for C$_{23}$H$_{24}$N$_4$O$_4$·1/3H$_2$O:
Calculated: C, 64.79; H, 5.83; N, 13.14
Found: C, 64.65; H, 5.58; N, 13.18.

EXAMPLE 15

Preparation of Ethyl β(S)-[[[[1-[4-(amino(hydroxyimino)-methyl)phenyl]-2-oxo-3(S)-pyrrolidinyl]amino]carbonyl]-amino]benzenepropanoate.

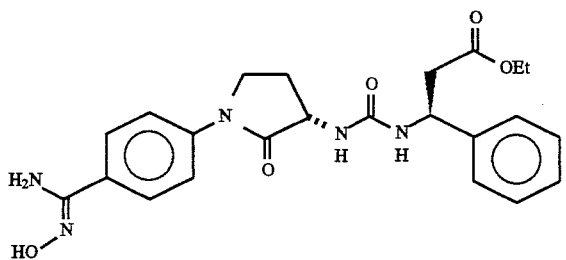

The title compound was prepared from the product of example 14 (450 mg, 1.07 mmol) in a manner similar to example 6 affording 431 mg (89%) of product [m.p. 192°–193° C. (dec.)]. $^1$H-NMR (300 MHz, d$_6$-DMSO) δ 1.10 (t, J=7Hz, 3H), 1.87 (m, 1H), 2.49 (m, 1H), 2.77 (m, 2H), 3.74 (m, 2H), 4.00 (q, J=7Hz, 2H), 4.41 (m, 1H), 5.10 (m, 1H), 7.20–7.40 (m, 5H), 7.69 (s, 4H).
Anal. calc'd. for C$_{23}$N$_{27}$N$_5$O$_5$·1/2H$_2$O:
Calculated: C, 59.73; H, 6.10; N, 15.14
Found: C, 59.67; H, 6.38; N, 14.85.

EXAMPLE 16

Preparation of Ethyl β(S)-[[[[1-[4-(aminoiminomethyl)phenyl]-2-oxo-3(S)-pyrrolidinyl]amino]carbonyl]amino] benzenepropanoate Acetate.

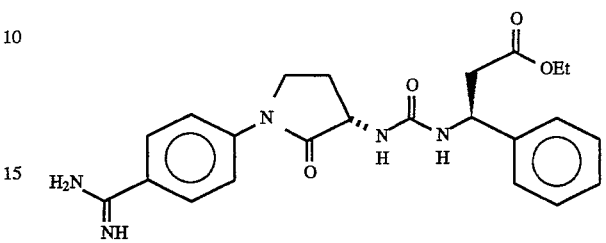

The title compound was prepared from the product of example 15 (400 mg, 0.88 mmol) in a manner similar to example 7 affording 335 mg (76%) of product [m.p. 210°–211° C. (dec.)]. $^1$H-NMR (d$_6$-DMSO) δ 1.14 (t, J=7Hz, 3H), 1.93 (s, 3H), 2.03 (m, 1H), 2.47 (m, 1H), 2.80 (m, 2H), 3.84 (m, 2H), 4.04 (m, 2H), 4.50 (m, 1H), 5.05 (t, J=7Hz, 1H), 7.23–7.44 (m, 5H), 7.92 (d, J=8Hz, 2H), 7.97 (d, J=8Hz, 2H).
Anal. calc'd. for C$_{25}$H$_{31}$N$_5$O$_6$ 1/2H$_2$O:
Calculated: C, 59.28; H, 6.37; N, 13.83
Found: C, 58.96; H, 6.21; N, 13.92.

What is claimed is:
1. A compound of the formula

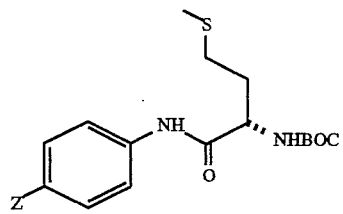

wherein Z is selected from the group consisting of H, —CN, —CONH$_2$ and —CO$_2$alkyl and BOC is t-butoxycarbonyl.

* * * * *